United States Patent [19]

Isshiki et al.

[11] 4,347,383

[45] Aug. 31, 1982

[54] PROCESS FOR PRODUCING BENZOPHENONE-AZINES

[75] Inventors: Tomiya Isshiki; Tetsuo Tomita, both of Tokyo; Shuzabu Sakaguchi, Matsudo; Toshiaki Kohzaki, Matsudo; Osamu Aoki, Matsudo; Norio Takeda, Matsudo; Yoshiyuki Aoki, Tokyo, all of Japan

[73] Assignee: Mitsubishi Gas Chemical Company, Inc., Tokyo, Japan

[21] Appl. No.: 147,194

[22] Filed: May 6, 1980

[30] Foreign Application Priority Data

May 11, 1979 [JP] Japan .................................. 54-57707
Feb. 1, 1980 [JP] Japan .................................. 55-11304

[51] Int. Cl.³ .......................................... C07C 109/16
[52] U.S. Cl. .................................................. 564/249
[58] Field of Search ........................................ 564/249

[56] References Cited

U.S. PATENT DOCUMENTS 2,870,206  1/1959  Meyer et al. .......................... 564/249
4,079,080  3/1978  Hayashi .................................. 564/249
4,233,242  11/1980  Nagato et al. ........................ 564/249

OTHER PUBLICATIONS

Kume, Hidetoshi et al. *Chemical Abstracts*, vol. 92, #110681e (1980) (Japanese 79,125,629–Sep. 29, 1979.
Kirk–Othmer "Encyclopedia of Chemical Technology," 2nd Ed., 1965 & 1966, vol. 5, p. 741 and vol. 6, p. 274.

*Primary Examiner*—Natalie Trousof
*Assistant Examiner*—L. Hendriksen
*Attorney, Agent, or Firm*—Browdy and Neimark

[57] ABSTRACT

A process for producing a benzophenone-azine which comprises reacting the corresponding benzophenone-imine with molecular oxygen or benzophenone with ammonia and molecular oxygen in the presence of a catalyst selected from the group consisting of metals, metal oxides and alloys of two or more metals, particularly copper or copper alloy-containing catalyst, is disclosed.

4 Claims, 1 Drawing Figure

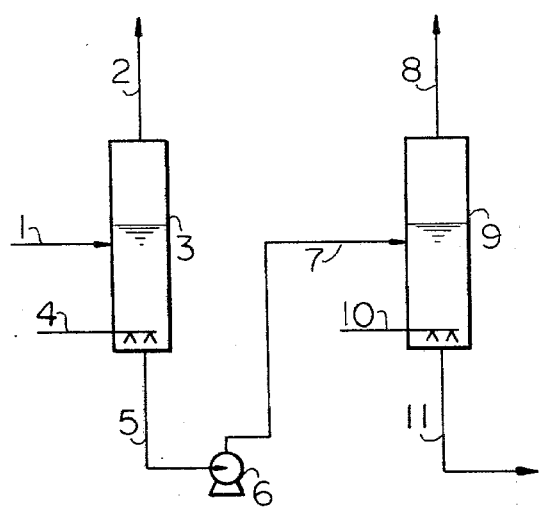

PROCESS FOR PRODUCING BENZOPHENONE-AZINES

BACKGROUND OF THE INVENTION

This invention relates to a process for producing a benzophenone-azine which is an intermediate used for producing hydrazine from benzophenones.

Many processes for producing benzophenone-azines by oxidizing benzophenone-imines are known in the art. A process for producing a benzophenone-azine by oxidizing benzophenone-imines in the presence of a copper halide, particularly cuprous chloride, is known from U.S. Pat. No. 2,870,206. A process for producing a benzophenone-azine by contacting a benzophenone in pyridines with ammonia and molecular oxygen in the presence of cuprous chloride and ammonium chloride or zinc chloride is known from Japanese Patent Publication (laid open) No. 7942/1977. A process for producing a benzophenone-azine by oxidizing a benzophenone-imine in the presence of excess amount of pyridine by using copper (II) halide methoxide is known from Japanese Patent Publication (laid open) No. 147047/1978. Japanese Patent Publication (laid open) No. 71045/1978 discloses that copper acetates, copper thiocyanade, copper cyanide and the like are useful for preparing benzophenone-azines from benzophenone-imines. Japanese Patent Publication (laid open) No. 131987/1977 (U.S. Pat. No. 4,079,080) discloses that a high molecular catalyst obtained by incorporating cuprous halide in a resin, the functional group of which is pyridines, is useful for oxidizing benzophenone-imines.

However, these processes need expensive copper salt as a catalyst. When copper salts are used as liquid phase homogeneous catalyst, it is necessary to control the valency of the copper, to keep the ratio of copper ion to negative ion constant, or to introduce a ligand, such as expensive pyridine, into the catalyst for preventing the decrease in the reaction activity. In addition, since the prior catalyst is dissolved in the reaction solution, the prior processes need complicated operations to recover copper salt as a catalyst from the solution. For example, operations such as separation of the copper salt from the solution and regeneration of the copper catalyst, etc. are necessary. So, the process increases the investment of equipment and incurs a loss of energy for operation. Further, expensive anticorrosive material should be used for making equipment in order to prevent corrosion of the equipment by halogen constituting the catalyst. Accordingly, the processes are unsuitable from an industrial point of view.

When high molecular catalyst coordinated copper ion by a ligand, functional group of which is pyridines is used, copper ion is released from the catalyst during the reaction and is not completely on the catalyst even at the end of the reaction. The process is not proper in spite of using a particular resin.

SUMMARY OF THE INVENTION

Research has now been carried out for a process practicable for producing benzophenone-azines industrially. As a result, it has been found that a metal or a metal oxide is a useful catalyst for producing benzophenone-azines from benzophenone-imines.

Therefore, an object of this invention is to provide a practicable industrial process for producing a benzophenone-azine from a benzophenone-imine.

This invention relates to a process for producing a benzophenone-azine having the formula

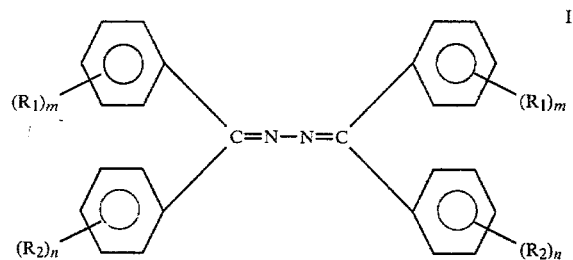

wherein $R_1$ and $R_2$ may be the same or different, and each of $R_1$ and $R_2$ are independently aliphatic alicyclic or aromatic hydrocarbon having 1-10 carbon atoms,

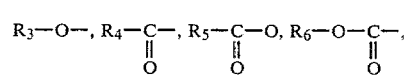

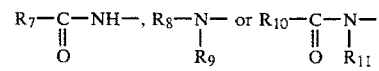

wherein $R_3$, $R_4$, $R_5$, $R_6$, $R_7$, $R_8$, $R_9$, $R_{10}$ and $R_{11}$ are independently alkyl having 1-10 carbon atoms; halogen; hydroxy; nitro; or cyano; or $R_1$ and $R_2$ when taken together from a single bond or substituted or unsubstituted methylene wherein the substituent is methyl; m is 0 or integer of 1-5; and n is 0 or integer of 1-5 which comprises reacting (a) a benzophenone-imine having the formula

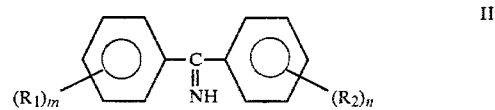

wherein $R_1$, $R_2$, m and n are as defined above with molecular oxygen, or (b) a benzophenone having the formula

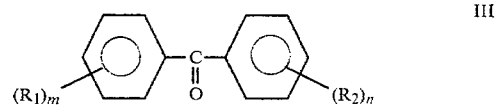

wherein $R_1$, $R_2$, m and n are as defined above with ammonia and molecular oxygen in the presence of a catalyst containing at least one material selected from the group consisting of metals, metal oxides and alloys of two or more metals.

FIG. 1 is flow sheet of the reaction in Example 52, The elements are: supply pipe for benzophenone-imine 1, pipes for discharging air 2 and 8, first reactor 3, pipes for introducing air 4 and 10, pipes for discharging reaction solution 5 and 11, pump 6, pipe for introducing reaction solution 7 and second reactor 9.

The benzophenone-imine may be prepared by reacting a benzophenone having the formula

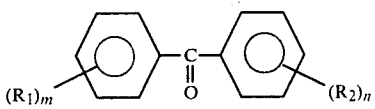

III wherein $R_1$, $R_2$, m and n are as defined above with ammonia and molecular oxygen, but it may be prepared by other methods from raw materials other than benzophenones.

Example of benzophenones employed in the practice of this invention include benzophenone, 2-, 3- or 4-methylbenzophenone, 2-, 3- or 4-ethylbenzophenone, 2-, 3- or 4-n-propylbenzophenone, 2-, 3-, or 4-isopropylbenzophenone, 2-, 3- or 4-n-butylbenzophenone, 2-, 3- or 4-iso-butylbenzophenone, 2-, 3- or 4-tert.-butylbenzophenone, 2-, 3- or 4-amylbenzophenone, 2-, 3- or 4-decylbenzophenone, 2-, 3- or 4-methoxybenzophenone, 4-cyclohexylbenzophenone, 4-phenylbenzophenone, 2,4-dimethylbenzophenone, 2,3-dimethylbenzophenone, 3,4-dimethylbenzophenone, 2,4-diethylbenzophenone, 2,3-diethylbenzophenone, 3,4-diethylbenzophenone, 2-methyl-4-ethylbenzophenone, 2-methyl-4-butylbenzophenone, 2,2'-, 3,3'-, 4,4'-, 2,3'-, 2,4'- or 3,4'-dimethylbenzophenone, 2-, 3- or 4-chlorobenzophenone, 2-chloro-4-methylbenzophenone, 4-chloro-4'-methylbenzophenone, 4,4'-dichlorobenzophenone, 4-nitrobenzophenone, 2,4-dinitrobenzophenone, 4-hydroxybenzophenone, 4-N,N-dimethylaminobenzophenone, 4-acetylbenzophenone, 4-methoxycarbonylbenzophenone, 4-N,N-dimethylcarbamoylbenzophenone, 4-hydroxybenzophenone, 4-cyanobenzophenone, fluorenone, anthron and 10-methyl anthron. Other benzophenones are also usable in the practice of this invention.

The benzophenones having the formula

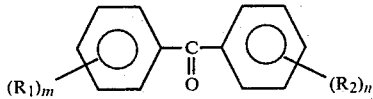

wherein $R_1$ and $R_2$ are as defined above and m and n are 0 or integer of 1 or 2 are preferable. Benzophenones having molecular weight ranging from 182 to 310 are suitable for preparing intermediate for hydrazine. The benzophenones of formula III wherein $R_1$ and $R_2$ is aliphatic hydrocarbon having 1–5 carbon atoms, halogen or nitro, and m and n is 0, 1 or 2 are more preferable. Examples of preferred benzophenons include methylbenzophenone, ethylbenzophenone, propylbenzophenone, butylbenzophenone, amylbenzophenone, dimethylbenzophenone, methylethylbenzophenone, diethylbenzophenone, methylpropylbenzophenone, dipropylbenzophenone, dibulbenzophenone, diamylbenzophenone, chlorobenzophenone, nitrobenzophenone, dipropylbenzophenone, dibutylbenzophenone, diamylbenzophenone and fluorenone.

The benzophenone-imines corresponding to the above mentioned benzophenones are usable in the practice of this invention. The benzophenone-imines corresponding to the above mentioned preferred benzophenones are prepared in this invention. The benzophenone-imines corresponding to the above mentioned more preferred benzophenones are also more preferred in this invention.

The benzophenone-imines represented by formula II may be prepared by reacting the above benzophenones with ammonia in the presence of the present catalyst or other catalysts, by reacting benzonitrile with aryl magnesium bromide which is Gringnard reagent or by dehydrating diaryl aminoalcohol. The present catalyst is not only effective oxidizing benzophenone-imines with oxygen, but also is effective for oxidizing benzophenone-imines while converting benzophenones to the corresponding imines in a reactor. For example, when the benzophenones of formula III react with ammonia and molecular oxygen using the present catalyst, benzophenone-azines are formed through benzophenone-imines.

The catalysts employed in the practice of this invention may be preferably selected from the group consisting of (a) metals belonging to Groups Ib, IIb, IIIb, IVb, Vb, VIb, VIIb and VIII and fourth, fifth and sixth periods of the Periodic Table, (b) metals belonging to Groups IIIa, IVa, Va and VIa and fifth and sixth period of the Periodic Table, (c) oxides of one or more of these metals and (d) alloys of two or more of these metals. The metal, the metal oxide or the metal alloy is usable alone, or combination thereof is usable.

Of these catalysts, Cr, Mn, Fe, Co, Ni, Tl, Pb, Cu and Ag; oxides of these metals and alloys of these metals are more preferable. The preferable catalysts include nickel monoxide, trinickel tetroxide, dinickel trioxide, cobalt monoxide, tricobalt tetroxide, dicobalt trioxide, iron monoxide, iron (II) iron (III) oxide, iron (III) oxide, dichrome trioxide, chrome dioxide, dichrome pentoxide, manganese monoxide, dimanganese trioxide, trimanganese tetroxide manganese dioxide, copper monoxide, dicopper oxide, copper, silver monoxide, silver, dithallium trioxide, dithallium monoxide, lead monoxide, trilead tetroxide, and lead dioxide.

A catalyst containing copper or alloy of copper is most preferable as a catalyst for preparing a benzophenone-azine from the corresponding benzophenone-imine or benzophenone. A catalyst composed of copper may be electrolytic copper, oxygen free copper, reduced copper obtained by reducing copper oxide, cuprous oxide, copper carbonate, copper hydroxide, copper sulfate, copper chloride, copper nitrate, copper acetate, copper thiocyanate, copper sulfide, basic copper carbonate, copper phosphate with a reducing agent; and metallic copper obtained by developing Raney copper.

Catalysts composed of alloys of copper and other metals include alloys of copper and zinc, tin, aluminium, iron, nickel, manganese, silicon, lead, antimony, gold, silver, palladium, rhodium, iridium, and the like. Examples of the alloys include 7-3 brass, 6-4 brass, red brass, Naval brass, Alumi brass, Albrac, Raney copper, phosphor bronze, cupro-nickel 30%, white copper, nickel silver, silicon bronze, aluminum bronze, bronze castings, Silzin bronze, and the like.

The catalysts employed in this invention can be prepared by various methods in order to increase activity of the catalyst and selectivity of the reaction. For example, in order to increase surface area of catalyst and activity of catalyst and to improve selectivity of reaction, the catalyst can be carried on a carrier. Any carrier which does not inhibit the reaction and which is stable under the reaction conditions can be used in the present invention. Examples of such carriers include activated carbon, asbestos, diatomaceous earth, magnesium hydroxide, silicagel, silicon carbide, Celite (trade name of product of Johns-Manville Co.), alumina, silica-alumina, aluminamagnesia, titanium oxide (rutile), pumice, bauxite, alundum, corundum, glass powder, cements, zeolite, molecular sieve, brick, boria, thoria, barium sulfate, spinel, clay, talk, gypsum, and resins having heat-resistance and oridation-resistance.

When an oxide of a single metal is used as a catalyst, metal, and hydroxide, carbonate, nitrate, halides, sulfite, organic acid salts, such as formate, acetate and oxalate, and the like of the metal is calcined to form a metal oxide. Alternatively, the metal and these metal salts react with an oxidant, such as hydrogen peroxide, peracetic acid, oxygen, air, ozone, sodium hypochlorite, potassium hypochlorite, sodium peroxide, barium peroxide, performic acid, permaleic acid, benzoyl peroxide, methyl ethyl ketone peroxide, pertoluic acid, chlorine, nitric acid, aqua regia or the like to form metal oxides. When a metal or metals are used as a catalyst, the oxide or salt of the metal may be reduced with a reductant such as hydrogen, formalin, formic acid, hydrazine, sodium borohydride, carbon monoxide, hydrosulfite, sodium sulfite, or the like to form a metal catalyst. Alternatively, the metal oxide or metal salt may be reduced by electrolytic reduction or ionization.

When oxides of two or more metals are used as a catalyst, the mixture of metals or mixture of salts of metals obtained by blending, coprecipitation or the like is calcined to form oxides of metals. Alternatively, the mixture of metals or mixture of metal salts reacts with the oxidant to form oxides of metals. Mixture of metal oxide or mixture of metal salts react with the reductant to form a metal or an alloy.

In order to hold the metal or mixture of metals, or the metal oxide of mixture of metal oxides on a carrier by means of conventional procedure, the said oxidation or reduction is usable after coprecipitation, impregnation, ion exchange and blending.

A copper catalyst is carried on a carrier by dispersing and dissolving metallic copper, copper oxide, a copper complex or a copper salt in water. The carrier is added to the solution to blend the mixture. The copper or copper compound is carried on a carrier through evaporation to dryness, impregnation, coprecipitation, adsorption or ion exchange. If necessary, the copper compound carried on a carrier is reduced in a liquid or gaseous phase with a reducing agent, such as formaldehyde, formic acid, hydrazine, hydrogen, carbon monoxide, hydrosulfite, sodium sulfite, sodium boron hydride, by electrolytic reduction or by difference of ionization tendency. Alternatively, coprecipitation catalyst containing copper may be prepared by the following: Metallic copper, copper oxide, a copper complex or a copper salt is dispersed or dissolved in water with at least one of salts of metals other than copper, such as sulfate, halides, nitrate, phosphate, carbonate, organic acid salts of heavy metal selected from aluminum, antimony, arsenic, barium, bismuth, cadmium, cobalt, gold, iridium, gallium, germamium, iron, lanthanum, lead, magnesium, manganese, mercury, molybdenum, nickel, niobium, osmium, palladium, rhodium, ruthenium, silver, strontium, thallium, thorium, tin, tungsten, vanadium, zinc, zirconium or tantalum. A precipitating agent, such as sodium hydroxide, potassium hydroxide, sodium bicarbonate, potassium bicarbonate, sodium carbonate, potassium carbonate, ammonium carbonate, barium hydroxide, calcium hydroxide, sodium sulfide, ammonium sulfide, magnesium hydroxide, sodium phosphate, sodium aluminate or sodium silicate is added to the dispersion or the solution to coprecipitate copper and other metal. The coprecipitate is separated from the dispersion or the solution, and dried or calcined. In some cases, the dried or calcined coprecipitate may be powdered and be formed into granulate with a bonding agent, such as graphite. The coprecipitate is reduced with a reductant, or through electrolytic reduction or ionization tendency to form a coprecipitation catalyst containing copper.

When the catalyst employed in the present invention is in a high oxidized state, it tends to exhibit high activity. But, even through the catalyst is in a metallic state or in low oxidized state, it exhibits activity. In addition, it is unnecessary to use pure metal or metal oxide as a catalyst, and the catalyst may contain the compounds of hydroxide, halide, sulfide, phosphate, carbonate, sulfate, silicate, borate, phosphide, nitrate, formate, oxalate and acetate, and the compound being capable of forming metals or metal oxides under the reactions is also useful as a catalyst.

In order to increase the activity or the selectivity of the reaction, the present catalyst may contain the co-catalyst, such as hydroxide, halides, sulfide, phosphide, carbonate, nitrate, silicate, borate, sulfate, phosphate, formate, acetate or oxalate of alkali metal (Ni, K, Na, Pb, Ce) or alkali earth metal (Be, Mg, Ca, Sr); ammonium salts, such as ammonium carbonate, ammonium chloride, ammonium phosphate, ammonium formate and ammonium acetate; boron, phosphor, sulfur, silicon, or oxide, hydride, halides or sulfide of these elements; or Al, Ge, Ga, As, Se or hydroxide, halides, sulfide, phosphate, carbonate, nitrate, sulfate, formate, acetate and oxalate of these elements. When the co-catalyst is used alone, the catalytic action thereof is weak.

The catalyst of this invention is used alone or is used in the form carried on a carrier, and may be in a state of particle, powder, fiber or spongy. The state of the catalyst depends on state of the reaction system. For example, particulate catalyst is preferably used in a fixed bed, depending on its form, its density, and its size. The powdered catalyst is preferably dispersed into the liquid reactants or is used in a fluidized bed.

The amount of catalyst employed is not critical. In general, the catalyst may be used in amount of 0.001 to 50% by weight, preferably 0.01 to 30% by weight and more preferably 0.05 to 20% by weight on the basis of weight of benzophenone-imine. The reaction conditions under which the oxidation reaction of benzophenone-imine is carried out depend on activity of catalyst employed nad state of the reaction system. In general, the reaction temperature is in the range of 60° to 300° C., preferably 70° to 250° C. and more preferably 90° to 230° C. The reaction time depends on activity and a degree of conversion of the catalyst. In general, the time is in the range of 0.1 hour to several tens of hours.

The molecular oxygen may include pure oxygen, oxygen enriched gas and mixture of oxygen and nitrogen, namely air. The reaction pressure may be reduced pressure, one atmospheric pressure or superpressurized pressure. In general, when oxygen alone is used as molecular oxygen, the reaction pressure is in the range of 0.1 to 20 atms. When air is used as molecular oxygen, the reaction pressure is in the range of 0.1–40 atms.

The way of introducing oxygen or an oxygen-containing gas into the reaction system is not critical. The oxygen gas or oxygen-containing gas may be introduced into the reaction system by blowing the gas into the liquid continuously, or it may be present as a superpressurized gas in an enclosed reaction system containing the ligand. Preferably, the molecular oxygen is blown into the liquid reagents in order to prevent hydrolysis of benzophenone-imines. It is preferable to use dry oxygen gas or dry oxygen-containing gas as molecular oxygen.

The reaction method may be continuous or batchwise. In order to increase the rate of reaction, it is preferable to use multi-vessel continuous process, so called cascade process.

The reaction of this invention proceeds without using any solvent. A solvent may be used in order to promote dissolution of the benzophenone-azines or to keep the reaction system in a solution state.

It is preferable to use a solvent which is not subjected to decomposition in the ammoxydation of benzophenones and promotes dissolution of the benzophenone-azines formed by oxidation reaction of benzophenone-imines and which does not mix well with water. Examples of the solvents include benzene, toluene, o-, m- or p-xylene, ethylbenzene, mesitylene, cumene, pseudocumene, amylbenzene, aromatic hydrocarbons having 6-16 carbon atoms and mixtures thereof, chlorobenzene, o-, m- or p-dinitrobenzene, o-, m- or p-chlorotoluene, diphenyl, phenanthrene, anisole, diphenyl ether, acetophenone, dibenzyl, benzophenone, hexane, heptane, cyclohexane, cyclooctane, ethylcyclohexane, ethylene dichloride, tetrachloroethylene, diisopropyl ether, butyl acetate, butyl benzoate, phenyl benzoate, dimethyl phthalate and the like.

It is preferable in the present invention to use benzophenone-imines obtained from benzophenones. In this case, unreacted benzophenone acts as a solvent.

The catalyst employed in this invention is a heterogeneous system catalyst, i.e. an insoluble catalyst, so the catalyst can be recovered by a simple operation, regenerated and reused. Regeneration of the catalyst can be easily performed for increasing selectivity of reaction and reaction rate. So, the present process is advantageous from an industrial point of view.

The present invention is further illustrated by the following Examples. However, this invention is not limited by these examples, and changes and modifications within the spirit and scope of this invention can be effected. Yield is by mol percent. In these examples, selectivity means ratio of mol of object product obtained to mol of raw material reacted. The percents and parts on proportion of components are by weight, unless otherwise specified.

EXAMPLE 1

Into a reactor was charged 30 gr. (imine 44.1 milli mol) of benzophenone-imine (26.6% pure; the remainder was benzophenone). While blowing nitrogen from a supply pipe inserted at the bottom of the reactor, the solution was heated to 200° C. To the solution was added 0.6 gr. (3.63 milli mol) of commercially available powdered dinickel trioxide (catalyst). Thereafter, oxygen was blown from the pipe at one atmospheric pressure for 3 hours as speed of 100 ml/min. with stirring. After 3 hours, the reaction product was analyzed by gas chromatography. The analysis showed that benzophenone-azine was formed in yield of 54% (11.9 milli mol) and in selectivity above 99%.

The formation of benzophenone-azine was confirmed by the following procedure. The catalyst was removed from the reaction solution by means of glass filter at 100° C. Ethanol was added to the filtrate to form crystalline material. The materials was removed by glass filter. The material was washed with ethanol and then dried at a reduced pressure. The resulting material was a light yellow powder with a melting point of 163°-164° C. In a certain publication, melting point given for benzophenone-azine is 162° C. Mass spectrum, infrared spectrum and nuclear magnetic resonance spectrum of the material were the same as those of benzophenone-azine.

EXAMPLE 2

The procedure of Example 1 was repeated except that 0.6 gr. (1.3 milli mol) of commercially available powdered dithallium trioxide was used as a catalyst. Benzophenone-azine was formed in a yield of 89% (19.6 milli mol). Selectivity was above 99%.

EXAMPLE 3

The procedure of Example 1 was repeated except that 1.2 gr. (7.26 milli mol) of powdered dinickel trioxide was used as a catalyst. Benzophenone-azine was formed in a yield of 84% (18.5 milli mol).

EXAMPLE 4

The procedure of Example 2 was repeated except that the reaction temperature was 160° C. Benzophenone-azine was formed in a yield of 30% (6.6 milli mol).

EXAMPLE 5

The procedure of Example 3 was repeated except that air was used in place of oxygen. Benzophenone-azine was formed in a yield of 38% (8.4 milli mol).

EXAMPLE 6

The procedure of Example 1 was repeated except that 0.6 gr. (1.41 milli mol) of powdered dithallium monoxide was used as a catalyst. Benzophenone-azine was formed in a yield of 44% (9.7 milli mol).

EXAMPLES 7-11

The procedure of Example 3 was repeated using the metal oxides shown in Table 1 as a catalyst respectively. The results are shown in Table 1.

TABLE 1

| Ex. No. | Metal oxide (catalyst) kind | amount (gr.) | Yield of benzophenone-azine (%) |
|---|---|---|---|
| 7 | dicobalt trioxide | 1.2 | 76 |
| 8 | lead dioxide | 1.2 | 52 |
| 9 | manganese dioxide | 1.2 | 40 |
| 10 | disilver oxide | 1.2 | 30 |
| 11 | vanadium pentoxide | 1.2 | 20 |

EXAMPLES 12-16

Into a 300 ml autoclave made of stainless steel were charged 10 grs. (28.7 milli mol) of benzophenone-imine (52% pure; the remainder was benzophenone), 50 ml of o-dichlorobenzone and 1.0 gr. of metal oxide as shown in Table 2 respectively. Oxygen was maintained in the autoclave at 12 Kg/cm$^2$, gauge at room temperature, and the solution was heated to 200° C. From this point, the reaction was continued for 2.5 hours with stirring. The results are shown in Table 2.

TABLE 2

| Example No. | Metal oxide (catalyst) | Yield of benzophenone-azine (%) |
|---|---|---|
| 12 | dithallium trioxide | 62.5 |
| 13 | dinickel trioxide | 43.8 |
| 14 | dicobalt trioxide | 26.3 |
| 15 | manganese dioxide | 21.0 |
| 16 | dichromium trioxide | 20.0 |

EXAMPLE 17

Commercially avilable powdered nickel hydroxide was calcined in an electric furnace at 340° C. for 5 hours in air. The nickel of the resulting catalyst was 67.7% (theoretical content of Ni in dinickel trioxide is 70.9%).

The procedure of Example 3 was repeated except that dinickel trioxide prepared as mentioned above was used. Benzophenone-azine was formed in a yield of 79% (17.4 milli mol).

EXAMPLE 18

Alpha-alumina was immersed in a 40% aqueous solution of nickel nitrate and impregnated with nickel nitrate. The nickel nitrate-impregnated alumina was added to a 10% aqueous solution of sodium carbonate. The nickel nitrate in the alumina was converted to nickel carbonate and nickel hydroxide. The nickel carbonate and nickel hydroxide were coprecipitated into the alumina.

The alumina was removed by glass filter and sufficiently washed with water. The alumina was dried at 120° C. for 5 hours in a drying chamber, and was calcined in an electric furnace at 260° C. for 3 hours in air.

The procedure of Example 1 was repeated except that 3 grs. of dinickel trioxide carried on alumina prepared by the above method was used as a catalyst. The amount of the compound carried as nickel was 3.3%. Benzophenone-azine was formed in a yield of 33% (7.3 milli mol).

EXAMPLE 19

8.0 grs. of nickel nitrate and 5.0 grs. of zinc nitrate were dissolved in 100 ml of distilled water. A 10% aqueous solution of ammonium carbonate was added dropwise to the mixture with stirring to precipitate nickel carbonate and zinc carbonate. The amount of ammonium carbonate added was 200 ml, and the time required for the addition was 1 hour. After adding, the mixture was allowed to stand overnight. The precipitate was filtered, washed with water, dried at 100° C. for 2 hours and then was calcined at 270° C. for 2 hours while passing air over the precipitate. The calcined material was crushed in a mortar to powder it. The nickel content of the powder was 43%.

The procedure of Example 1 was repeated except that 0.75 grs. of the above catalyst was used and the reaction time was 2 hours. Benzophenone-azine was formed in a yield of 63% (13.9 milli mol).

EXAMPLE 20

The procedure of Example 1 was repeated except that 0.6 grs. (4.2 milli mol) of commercially available powdered cuprous oxide was used and the reaction temperature was 2 hours. Benzophenone-azine was formed in a yield of 84.1% (18.5 milli mol).

EXAMPLE 21

Into a reactor was charged 30 grs. (imine 33.9 milli mol) of benzophenone-imine (benzophenone-imine 20.4%; the remainder was benzophenone). While blowing nitrogen from a supply pipe inserted at the bottom of the reactor, the solution was heated to 140° C. To the solution was added 0.6 grs. of commercially available powdered copper (produced by Wako Jun-yaku Co.). Thereafter, oxygen was blown from the pipe at one atmospheric pressure for 2 hours at speed of 100 ml/min. with stirring. After 2 hours, the reaction product was analyzed by gas chromatography. The analysis showed that benzophenone-azine was formed in yield of 59% (10.0 milli mol) and selectivity was above 99%.

EXAMPLE 22

Commercially available powdered copper was treated in a stream of hydrogen at 300° C. for 3 hours. The procedure of Example 21 was repeated except that the catalyst treated above was used. The catalyst was removed by filtering with a glass filter (G4). Colormetry analysis showed that the filterate contained copper. Gas chromatography of the reaction solution showed that benzophenone-azine was formed in a yield of 56% (9.5 milli mol).

EXAMPLE 23

The procedure of Example 21 was repeated except that air was used in place of oxygen. Benzophenone-azine was formed in a yield of 56% (9.5 milli mol).

EXAMPLE 24

The procedure of Example 21 was repeated except that the reaction temperature was 160° C. Benzophenone-azine was formed in a yield of 83% (14.1 milli mol).

EXAMPLE 25

Commercially available powdered cupric hydroxide was calcined at 500° C. for 5 hours in air and was reduced in a hydrogen stream at 300° C. for 3 hours.

The procedure of Example 21 was repeated except that 0.6 grs. of the catalyst prepared above was used. Benzophenone-azine was formed in a yield of 64% (10.8 milli mol).

EXAMPLE 26

The catalyst was prepared by using basic copper carbonate in place of cupric hydroxide in the same way as in Example 25.

The procedure of Example 25 was repeated except that the above catalyst was used and the reaction time was 3 hours. Benzophenone-azine was formed in a yield of 90% (15.3 mill mol).

EXAMPLE 27

100 grs. of a 24% aqueous solution copper nitrate and 176 grs. of a 10% aqueous solution of sodium carbonate were simultaneously added dropwise to 100 grs. of distilled water to form a precipitate. During the addition, the pH of the solution was maintained at 9. The time required for the addition was 2 hours.

After the addition, the mixture was allowed to stand overnight. Thereafter the predipitate was filtered and washed with water. The precipitate was dried at 110° C. for 5 hours and crushed in mortar to powder it.

The procedure of Example 25 was repeated except that the above catalyst was used and the reaction time was 3 hours. Benzophenone-azine was formed in a yield of 98% (16.6 milli mol).

EXAMPLE 28

To 100 grs. of water were simultaneously added dropwise 84 grs. of a 10% aqueous solution of sodium hydroxide and 100 grs. of a 24% aqueous solution of copper nitrate. During the addition, the pH of the solution was maintained at 10. The time required for the addition was 2 hours.

After the addition, the mixture was allowed to stand for 3 days. Thereafter, the precipitate was filtered and washed with water. The precipitate was dried at 110° C. for 5 hours and crushed in mortar to powder it.

The procedure of Example 25 was repeated except that the above catalyst was used and the reaction time was 3 hours. Benzophenone-azine was formed in a yield of 97%. (16.4 milli mol).

EXAMPLE 29

150 grs. of a 10% aqueous solution of copper sulfate was added dropwise to 150 grs. of a 10% aqueous solution of sodium carbonate with stirring to form a precipitate. At the end of the addition the pH of the solution was 8.2. The time required for the addition was 2 hours.

After the addition, the mixture was allowed to stand for 5 days. The precipitate was filtered and washed with water. The precipitate was dried at 110° C. for 5 hours, and crushed in a mortar to powder it.

The procedure of Example 25 was repeated except that the above catalyst was used and the reaction time was 3 hours. Benzophenone-azine was formed in a yield of 91% (15.4 milli mol).

EXAMPLE 30

A 10% aqueous solution of sodium hydroxide was added dropwise to 1000 grs. of a 2% aqueous solution of copper acetate with stirring to form a precipitate. At the end of the addition, the pH of the solution was 6.7. The time required for the addition was 2 hours.

After the addition, the mixture was allowed to stand for 4 days. Thereafter, the precipitate was filtered and washed with water. The precipitate was dried at 110° C. for 5 hours and crushed in a mortar to powder it.

The procedure of Example 25 was repeated except that the above catalyst was used and the reaction time was 3 hours. Benzophenone-azine was formed in a yield of 85% (14.4 milli mol).

EXAMPLE 31

A 2% aqueous solution of copper acetate was added dropwise to 100 grs. of a 10% aqueous solution of sodium carbonate with stirring at 65° C. to form the precipitate. At the end of the addition, the pH of the solution was 8.2. The time required for the addition was 2 hours.

After the addition, the mixture was allowed to stand for 4 days at room temperature. Thereafter, the precipitate was filtered and washed with water. The precipitate was dried at 110° C. for 5 hours and crushed in a mortar to powder it.

The procedure of Example 25 was repeated except that the above catalyst was used and the reaction time was 3 hours. Benzophenone-azine was formed in a yield of 97% (16.4 milli mol).

EXAMPLE 32

10 grs. of powdered Celite 545 (produced by Gasukuro Kogyo Co.) was dispersed in 70 grs. of a 40% aqueous solution of copper nitrate. Stirring was continued overnight. The solid material was filtered. The material was dried at 110° C. for 10 hours to obtain powder.

The procedure of Example 25 was repeated except that the above catalyst was used and the reaction time was 3 hours. Benzophenone-azine was formed in a yield of 82% (13.9 milli mol).

The catalyst copper content was 14%.

EXAMPLE 33

The procedure of Example 32 was repeated except that diatomaceous earth C-2 (produced by Gasukuro Kogyo Co.) was used in place of Celite. The yield of benzophenone-azine was 95% (16.1 milli mol).

The catalyst copper content was 14%.

EXAMPLE 34

Powdered Celite 545 was dispersed in 100 grs. of a 15.2% aqueous solution of copper nitrate to form a slurry. An aqueous solution of sodium carbonate (3 mol/l) was added dropwise to the slurry to adjust the pH of the solution to 8.3.

After the addition, stirring was continued for 15 minutes, and then the solid material was filtered, and washed with water. The material was dried at 110° C. for 5 hours.

The procedure of Example 25 was repeated except that the above catalyst was used and the reaction time was 3 hours. Benzophenone-azine was formed in a yield of 87% (14.7 milli mol).

EXAMPLE 35

The procedure of Example 21 was repeated except that gun metal was used, and the reaction time was 6 hours. The yield of benzophenone-azine was 37% (6.3 milli mol).

EXAMPLE 36

The procedure of Example 21 was repeated except that powdered brass was used, and the reaction time was 2 hours. The yield of benzophenone-azine was 5.0% (0.85 milli mol).

EXAMPLE 37

1.2 grs. of Raney copper (copper content of 50%) was developed with 4.4 grs. of a 30% aqueous solution of sodium hydroxide. The development temperature was in the range of 40°–60° C. and the development time was about 1 hour.

After developing, the solid material was filtered and washed with ethanol, and then washed with benzophenone-imine several times to form developed Raney copper.

The procedure of Example 21 was repeated except that the above catalyst was used and the reaction time was 2 hours. The yield of benzophenone-azine was 43% (7.3 milli mol).

EXAMPLE 38

24 grs. of copper nitrate and 12 grs. of magnesium nitrate were dissolved in 160 grs. of distilled water. A 10% aqueous solution of sodium carbonate was added dropwise to the mixture with stirring to form a predipitate. At the end of the addition, the pH of the solution was 9. The amount of sodium carbonate solution added was about 340 grs. The time required for the addition was 2 hours.

After the addition, the mixture was allowed to stand overnight and the precipitate was filtered and washed with water. The precipitate was dried at 110° C. for 5 hours and crushed in a mortar to powder it.

The procedure of Example 25 was repeated except that the above catalyst was used and the reaction time was 3 hours. Benzophenone-azine was formed in a yield of 76% (12.9 milli mol).

EXAMPLE 39

24 grs. of copper nitrate and 2.3 grs. of zinc nitrate were dissolved in 170 grs. of distilled water. A 20% aqueous solution of sodium hydroxide was added dropwise to the mixture with stirring to form a precipitate. At the end of the addition, the pH of the solution was 10. The time required for the addition was 2 hours.

After the addition, the mixture was allowed to stand 3 days and the precipitate was filtered and washed with water. The precipitate was dried at 110° C. for 5 hours and crushed in a mortar to powder it.

The procedure of Example 25 was repeated except that the above catalyst was used and the reaction time was 3 hours. Benzophenone-azine was formed in a yield of 85% (14.4 milli mol).

EXAMPLE 40

24 grs. of copper nitrate and 4.6 grs. of ferric nitrate of sodium hydroxide was added dropwise to the mixture with stirring to form a precipitate. At the end of the addition, the pH of the solution was 10. The time required for the addition was 2 hours.

After the addition, the mixture was allowed to stand 3 days and the precipitate was filtered and washed with water. The precipitate was dried at 110° C. for 5 hours and crushed in a mortar to powder it.

The procedure of Example 25 was repeated except that the above catalyst was used and the reaction time was 3 hours. Benzophenone-azine was formed in a yield of 76% (12.9 milli mol).

EXAMPLE 41

24 grs. of copper nitrate and 3.1 grs. of nickel nitrate were dissolved in 170 grs. of distilled water. A 20% aqueous solution of sodium hydroxide was added dropwise to the mixture with stirring to form precipitate. At the end of the addition, the pH of the solution was 10. The time required for the addition was 2 hours.

After the addition, the mixture was allowed to stand overnight and the precipitate was filtered and washed with water. The precipitate was dried at 110° C. for 5 hours and crushed in mortar to powder it.

The procedure of Example 25 was repeated except that the above catalyst was used and the reaction time was 3 hours. Benzophenone-azine was formed in a yield of 74% (12.5 milli mol).

EXAMPLE 42

Into a bubble column having diameter of 5.5 cm and height of 100 cm was continuously charged benzophenone-imine (24.1% pure; the remainder was benzophenone) at speed of 200 grs./hr. Air (15 Nl/min.) was continuously supplied from a sparger installed at the bottom of the column. 30 grs. of commercially available powdered copper was placed into the column. The reagent solution resided in the column for 3 hours. The pressure in the column was 4 Kg/cm² G and the liquid temperature in the column was maintained at 140° C. 30 grs. of commercially available powdered copper was charged into the column as a catalyst.

The reaction solution was discharged from the column through a filter installed in the column, thereby leaving the catalyst in the column. The reaction was continuously performed for 24 hours. Conversion of benzophenone-imine was 88% and yield of benzophenone-azine was 87% (116 milli mol).

EXAMPLE 43

The procedure of Example 21 was repeated except that 15.0 grs. (imin 41.6 milli mol) of benzophenone-imine (imine content is 50.2%; the remainder was benzophenone) was used as a starting material, and 15.0 grs. of o-dichlorobenzene was used as a solvent. The yield of benzophenone-azine was 61% (12.7 milli mol).

EXAMPLE 44

The procedure of Example 21 was repeated except that 30 grs. (imine 38.9 milli mol) of 4-methyl-benzophenone-imine (imine content is 25.3%; the remainder was 4-methyl-benzophenone) was used as a starting material and o-dichlorobenzene was used as a solvent. The yield of 4.4-dimethylbenzophenone-azine was 58% (11.3 milli mol).

EXAMPLE 45

The procedure of Example 22 was repeated except that commercially available powdered copper oxide was used in place of powdered copper. The yield of benzophenone-azine was 63% (10.7 milli mol).

EXAMPLE 46

The procedure of Example 22 was repeated except that commercially available powdered cuprous oxide was used in place of powdered copper. The yield of benzophenone-azine was 65% (11.0 milli mol).

EXAMPLE 47

Commercially available powdered copper oxide weighing 4.0 grs. was dispersed in 75 ml of a 3.3% aqueous solution of hydrazine hydrate. The mixture was maintained at 80° C. for one hour with stirring. The solid material was filtered and washed with water, and further washed with acetone and dried under vacuum at room temperature.

The procedure of Example 21 was repeated except that 0.6 grs. of the above catalyst was used. The yield of benzophenone-azine was 74% (12.5 milli mol).

EXAMPLE 48

The procedure of Example 47 was repeated except that 2.5 grs. of commercially available powdered basic copper carbonate was used in place of powdered copper oxide. The yield of benzophenone-azine was 71% (12.0 milli mol).

EXAMPLE 49

The procedure of Example 47 was repeated except that 2.0 grs. of commercially available powdered basic copper carbonate was used in place of copper oxide. The yield of benzophenone-azine was 67% (11.4 milli mol).

EXAMPLE 50

The procedure of Example 21 was repeated except that 0.06 grs. of commercially available powdered copper was used. The yield of benzophenone-azine was 46% (7.8 milli mol).

EXAMPLES 53–55

The procedures of Example 21 were repeated except that the raw materials as given in Table 3 were used respectively. The reaction conditions and results are shown in Table 3.

TABLE 3

| Example No. | Raw material Kind | Amount employed | Reaction time (hr.) | Object product Kind | Yield % (mill Mol) |
|---|---|---|---|---|---|
| 53 | 4-tert.-butyl-benzophenone-imine (imine content 22.3%; remainder is 4-tert.-butyl-benzophenone) | 30 grs. (imine content 27.9 milli mol) | 3 | 4,4'-di-tert.-butylbenzo-phenone-azine | 72 (10.1) |
| 54 | 3-chlorobenzophenone-imine (imine content 19.8%; remainder is 3-chlorobenzophenone | 30 grs. (imine content 27.2 milli mol) | 5 | 3,3'-di-chlorobenzo-phenone-azine | 69 (9.4) |
| 55 | 3,4-dimethylbenzo-phenone-imine (imine content 21.6%; remainder is 3,4-dimethylbenzo-phenone-imine | 30 grs. (imine content 30.6 milli mol) | 5 | 3,3',4,4'-tetramethyl-benzophe-none-azine | 72 (11.0) |

EXAMPLE 51

30 grs. (164.7 milli mol) of benzophenone was charged into a reactor and was heated to 200° C. Activated alumina (produced by Nishio Kogyo Kabushiki Kaisha A-11) (1.3 grs.) and commercially available powdered copper (0.6 grs.) were added to the benzophenone. A gaseous mixture of ammonia and oxygen (oxygen content 50% by volume) was blown into the solution from the bottom of the reactor at speed of 70 ml/min. at one atmospheric pressure for 3 hours with stirring. Benzophenone-azine weighing 5.8 grs. (16.1 mill mol) and benzophenone-imine weighing 1.5 grs. (8.3 milli mol) were formed.

EXAMPLE 52

Benzophenone-azine was synthesized using apparatus as shown in the flow sheet of FIG. 1. Into each of 5.5 cm (inside diameter)×100 cm (height) bubble columns 3 and 9 equipped with gas disperger and filter for catalyst were charged 30 grs. of commercially available powdered copper and 600 grs. of benzophenone-imine (imine 24.1%, the remainder is benzophenone) as a raw material. The reaction was continuously carried out in the two columns at 140° C. at 4 Kg/cm².G.

Benzophenone-imine was supplied into bubble column 3 through pipe 1 at rate of 200 grs. hr. and air was introduced into column 3 through pipe 4 at rate of 15 Nl/min. The reaction solution was discharged from pipe 5 through the filter. The reaction was continuously carried out so that the raw material resides in column 3 for 3 hours.

The reaction solution discharged from column 3 was supplied into column 9 through pipe 7 and air was introduced into column 9 through pipe 10 at a rate of 15 Nl/min. The reaction solution was discharged from pipe 11 through a filter. The reaction was continuously carried out so that the raw material resided in the column 9 for 3 hours. Said operation was continued for 48 hours. Benzophenone-azine was obtained from pipe 11 in a yield of 98% (130 milli mol).

What is claimed is:

1. A process for producing a benzophenone-azine having the formula:

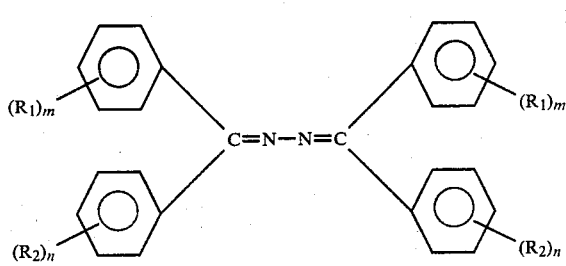

wherein $R_1$ and $R_2$ may be the same or different, and each of $R_1$ and $R_2$ is independently an aliphatic hydrocarbon radical having 1–5 carbon atoms or halogen; m is 0 or integer of 1–5; and n is 0 or integer of 1–5;

said process comprising reacting (a) a benzophenone-imine having the formula:

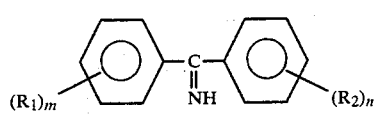

wherein $R_1$, $R_2$, m, and n are as defined above with molecular oxygen; or (b) a benzophenone having the formula:

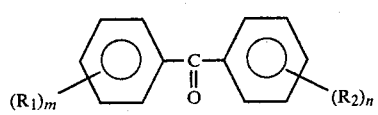

wherein $R_1$, $R_2$, m and n are as defined above with ammonia and molecular oxygen at temperature of 60°–300° C., said reaction being carried out in the presence of a catalyst containing at least one material selected from the group consisting of copper; copper alloys;

and metal oxides selected from the group consisting of oxides of Cr, Mn, Co, Ni, Tl, Pb, Cu, V and Ag.

2. The process as defined in claim 1 characterized by using a catalyst containing at least one material selected by the group consisting of copper, alloys of copper or mixtures thereof.

3. The process as defined in claim 2 wherein the catalyst is the one containing copper obtained by reducing copper oxide with a reducing agent.

4. The process as defined in claim 1 wherein said catalyst is selected from the group consisting of copper; copper alloys; and metal oxides selected from the group consisting of Cr, Mn, Ni, Pb, Cu and Ag.

* * * * *